(12) United States Patent
Mann

(10) Patent No.: US 6,558,656 B2
(45) Date of Patent: May 6, 2003

(54) ORAL AND TOPICAL COMPOSITIONS AND METHODS RELATED THERETO IN THE TREATMENT OF ACNE

(76) Inventor: Morris Mann, 21669 N. 57th Ave., Glendale, AZ (US) 85308

( * ) Notice: Subject to any disclaimer, the term of this patent is extended or adjusted under 35 U.S.C. 154(b) by 0 days.

(21) Appl. No.: 10/108,325

(22) Filed: Mar. 26, 2002

(65) Prior Publication Data

US 2002/0155171 A1 Oct. 24, 2002

Related U.S. Application Data

(60) Provisional application No. 60/198,687, filed on Apr. 20, 2000, and provisional application No. 60/285,098, filed on Apr. 19, 2001.

(51) Int. Cl.[7] .................................................. A61K 7/06
(52) U.S. Cl. ...................... 424/70.8; 424/401; 424/439; 424/464; 424/489; 424/70.1; 424/78.02; 424/78.03; 424/78.05; 424/78.07; 514/859; 514/860; 514/861; 514/863

(58) Field of Search .................................. 424/401, 464, 424/489, 70.1, 70.8, 78.02, 78.03, 78.05, 78.07; 514/859, 860, 861, 863

(56) References Cited

U.S. PATENT DOCUMENTS 5,952,314 A * 9/1999 DeMichele et al. ......... 426/567
6,030,948 A * 2/2000 Mann .......................... 514/12

* cited by examiner

*Primary Examiner*—Thurman K. Page
*Assistant Examiner*—Charesse Evans
(74) *Attorney, Agent, or Firm*—The Halvorson Law Firm

(57) ABSTRACT

Described are compositions and methods for the treatment of acne. The method and compositions comprise an orally ingested composition containing thymic peptides, vitamins, and minerals. Zinc, pantothenic acid, magnesium, pyridoxine, vitamins A and D, riboflavin, and folic acid are found to be essential to the composition. Also described is a topical composition comprising pantothenic acid that, when used in conjunction with the oral composition, resulted in a better response than either the oral or topical composition alone.

18 Claims, 4 Drawing Sheets

FIGURE 1

FORMULATION FOR THE ORAL TREATMENT OF ACNE

| Ingredients/Trade Name | Daily Dose | Weight % | Range Percent |
|---|---|---|---|
| Calcium Pantothenate | 3.0 gm | 71.43 | 1.0 – 99 |
| Riboflavin | 100 mg | 2.38 | 1.0 – 99 |
| Zinc sulfate | 200 mg | 4.77 | 1.0 – 99 |
| Magnesium Phosphate Tribasic | 400 mg | 9.54 | 1.0 – 99 |
| Folic Acid | 400 mg | 9.54 | 1.0 – 99 |
| Pyridoxine | 40 mg | 0.95 | 1.0 – 55 |
| Vitamin D | 1.1 mg | 0.026 | 0.001 – 50 |
| Vitamin A | 2.88 mg | 0.069 | 0.001 - 50 |
| Thymosin Fraction 5 | 50 mg | 1.19 | 0.001 - 85 |

The formula as noted is given as a daily dosage but may be divided into multiple capsules, tablets, servings, and the like.

FIGURE 2

FORMULATION FOR THE TOPICAL TREATMENT OF ACNE

| Composition | Percentage | Range |
|---|---|---|
| Pantothenic acid | 2 | 0.1-80 |
| Urea | 10 | 0.1-50 |
| Urea Peroxide | 2 | 0.1-50 |
| Propylene glycol | 82.75 | 1-99 |
| Phenoxyethanol | 3 | 0-80 |
| Fraction 5 | 0.25 | 0.001-50 |

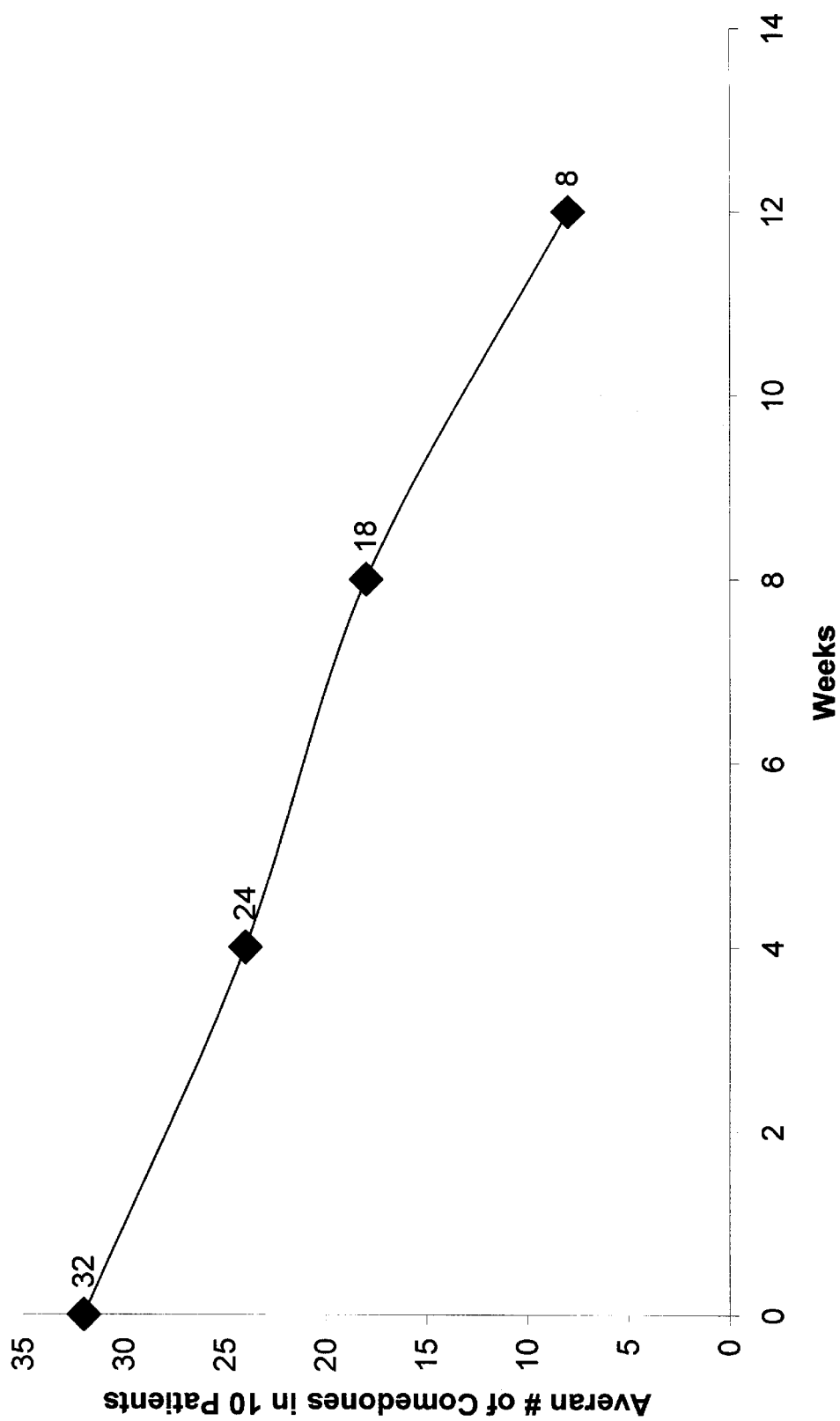
Figure 3 Oral Supplement

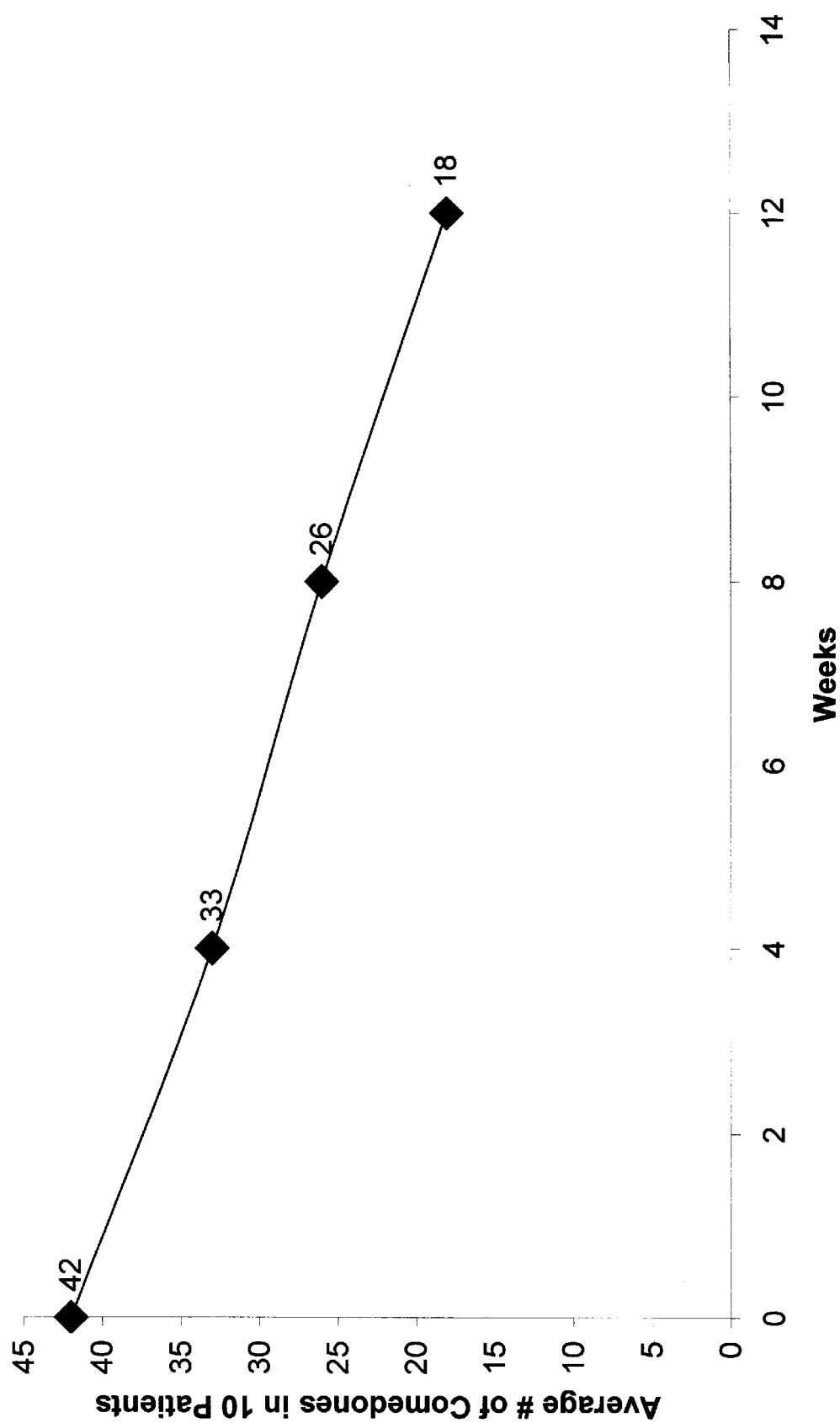

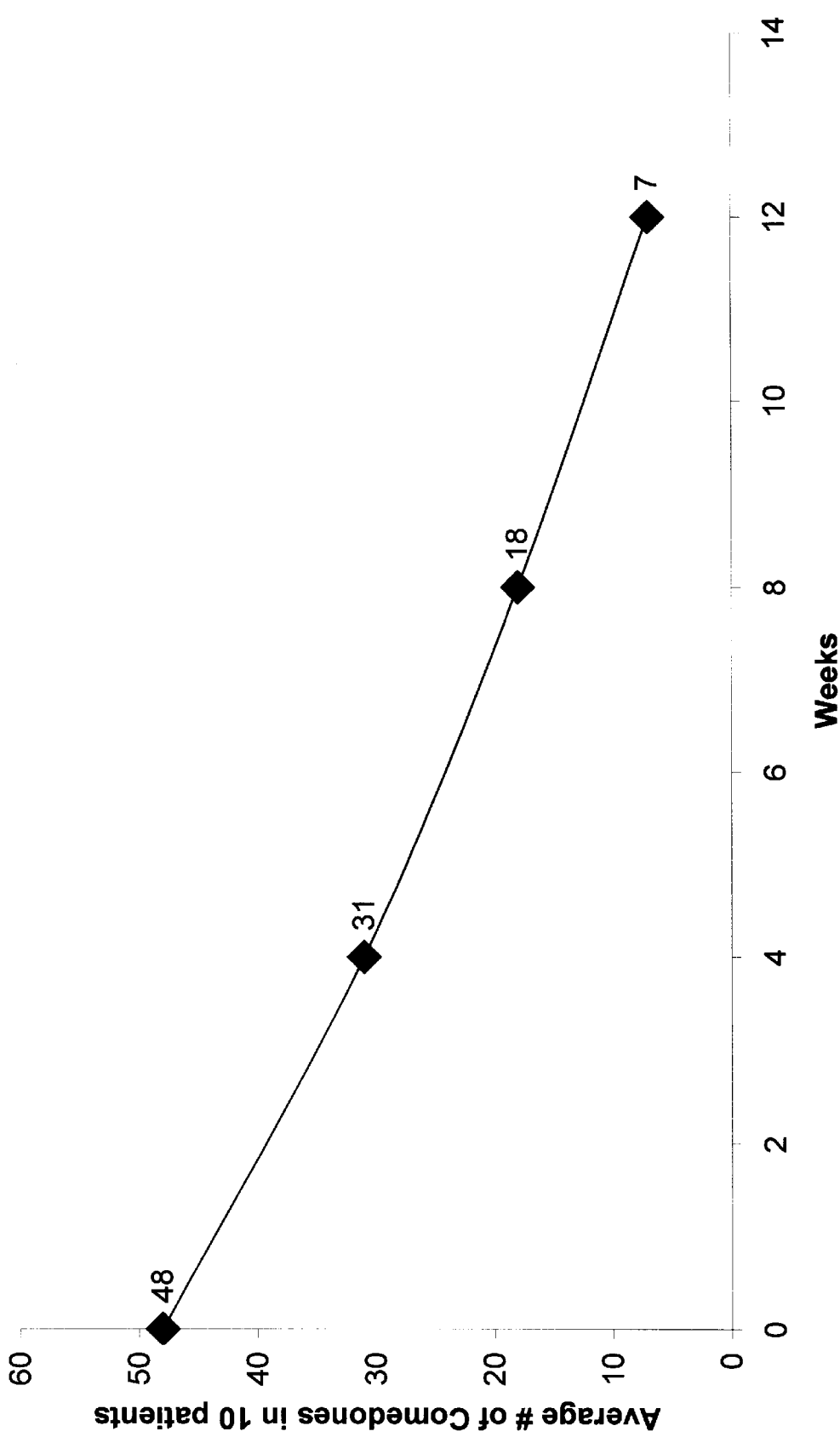

ORAL AND TOPICAL COMPOSITIONS AND METHODS RELATED THERETO IN THE TREATMENT OF ACNE

CROSS-REFERENCE TO RELATED APPLICATIONS

This applicant claims the benefit of U.S. Provisional Application No. 60/198,687, filed on Apr. 20, 2000 and U.S. Provisional Application No. 60/285,098, filed Apr. 19, 2001.

FIELD OF THE INVENTION

The present invention generally relates to oral and topical compositions and methods for the treatment of acne. More specifically, the present invention generally relates to compositions and methods for the treatment of acne by oral treatment with a composition comprising containing thymosin fraction 5 preparation plus other beneficial ingredients, such as vitamins and the like, and concomitant use of novel topical compositions.

BACKGROUND OF THE INVENTION

Acne is considered by those afflicted to be a serious problem. At some point 80% of all individuals, both male and female, experience acne. Although the vast majority of individuals afflicted with acne have spontaneous resolution of the problem over time, the effects of this skin disorder can be emotionally scarring. Some people, however, have active acne, until their mid-fifties. Likewise, in the last 20 years, for reason that are currently unknown, there has been a dramatic increase in acne affecting women over the age of 30.

Many causes have been proposed for acne. However, for a cause to have true validity, the treatment resolving the hypothesized cause must prove to be effective in the vast majority of cases. Causes that have been proposed include, but are not limited to: diet, hormonal disregulation, stress, bacterial overgrowth, heredity and environmental exposure; all of which may cause a deficiency of Coenzyme A. In no case has a treatment designed for any of the aforementioned causes proven to be uniformly effective. The only treatment that is proven effective in the vast majority of cases is the oral administration of isotretinoin (Accutane™). This medication, however, has numerous side effects; the most disturbing of which being its potential to induce sever birth defects.

Many topical approaches to the treatment of acne have been utilized. Topical medicaments currently available have proven to be effective in less severe cases, but none have been proven to be uniformly effective. These treatments have included antibiotics, benzoyl peroxide, vitamin A derivatives, such as retinoic acid, and many different epidermolytic agents; i.e. salicylic acid, glycolic acid ant the like. A unique anhydrous preparation was developed that effectively induced epidermolysis, while at the same time delivering a substantial amount of pantothenic acid to the affected area. It should be noted that normally pantothenic acid is unstable. However, due to the anhydrous nature of the formula, pantothenic acid is stabilized. These topical treatments typically require consistent use at least twice daily and recurrence after discontinuing therapy is quite high.

Although acne is not a systemic disease and is not in and of itself life threatening, it causes substantial emotional discomfort. Virtually all acne sufferers are willing to try any therapy that they think will be effective. Therefore, there exists a clear need in the art for a safe non-toxic method that will treat acne in the vast majority of cases without potentially dangerous side effects.

Many different therapeutic modalities have been proposed for the treatment of acne. With the exception of the vitamin A analog, isotretinoin, which is administered orally, none of these modalities have been proven to be uniformly effective. Isotretinoin exerts its effect against acne by decreasing sebum production.

For the vast majority of intrinsic acne, the cause is at least in part related to a deficiency in acetyl coenzyme A. This deficiency may be caused by a variety of different problems, i.e.: stress, diet, genetics, hormonal disregulation, environmental exposure, and the like.

Other treatment modalities that have been shown to be effective include zinc and pantothenic acid. Zinc was shown to be moderately effective at dosage levels of 100–300 mg per day. Pantothenic acid was shown to be effective at a dosage level of 10 grams per day. Very high doses of micellized Vitamin A have also been moderately effective. However, vitamin A has known toxicity when administered at high dosage levels.

SUMMARY OF THE INVENTION

An object of the present invention is to provide a composition that will increase the formation of Acetyl Coenzyme A. Surprisingly this composition is an orally administered combination of ingredients, in substantially lowered dosage requirements that otherwise described in extant literature.

It is another object of the present invention to provide a composition that will increase the formation of Acetyl Coenzyme A and include certain thymic peptides to substantially enhance the vitamin and mineral composition of the present invention. These peptides not only decrease the ability of bacteria to attach themselves, but also enhance the ability of the immune system to neutralize said bacteria. This is particularly important for cystic acne sufferers.

It is well known that pantothenic acid deficiencies result in a condition known as seborrheic dermatitis. In other words, due to a deficiency of pantohenic acid, there is a resultant increase in the production of sebum and a subsequent inflammation of the affected skin. Acne is nothing more than an exaggerated form of seborrheic dermatitis. Pantothenic acid deficiency invariably leads to a decrease in synthesis of acetyl coenzyme A, both systemically and in the skin proper.

A topical preparation was developed that significantly increased the delivery of pantothenic acid to the skin surface in an anhydrous vehicle, when used in conjunction with the oral preparation it was found to be surprisingly more effective than either the oral preparation or the topical preparation alone.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C.

§112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DESCRIPTION OF THE DRAWINGS

FIG. 1 is a table illustrating an example formulation for the oral composition according to the present invention.

FIG. 2 is a table illustrating an example formulation for the topical composition according to the present invention.

FIG. 3 illustrates the effectiveness of the oral composition of the present invention.

FIG. 4 illustrates the effectiveness of the topical composition of the present invention.

FIG. 5 illustrates the effectiveness of combined use of the oral and topical compositions according to the present invention.

DESCRIPTION OF THE PREFERRED EMBODIMENTS

The method and composition according to the present invention are useful for the treatment of acne.

Although many of the substances described in the subsequent text have been noted as useful in the treatment of acne in prior publications, and art, the composition noted herein is novel for its use of orally applied thymic fractions and from a dosage perspective, therefore the compositions described herein are more effective than any of the compositions previously known. Alternately, it has been found that in addition to the oral composition, additional topical application of a second formulation provides superior results.

Riboflavin, an essential water soluble B vitamin, is an integral component of the composition. To date there is no written literature in the art indicating the use of riboflavin in acne therapy. However, it should be noted that a riboflavin deficiency will result in seborrhea. Concomitantly, it should be that acne is always associated with an excessive production of sebum. Therefore, it stands to reason that at least part of the etilogy of acne may be a riboflavin deficiency.

Pantothenic acid has been used to treat acne in dosages of 10 gm per day. Although somewhat effective by itself, it is a massive dose and does not work well with cystic acne. Since for the vast majority of intrinsic acne the cause is at least in part related to a deficiency in Acetyl Coenzyme A. Pantothenic acid is necessary for the biosynthesis of Acetyl coenzyme A. The novelty within this invention is predicated on enhancing coenzyme A synthesis and secondarily on enhancing the immune system.

To enhance a person's Coenzyme A synthesis, it is necessary to have at least three components: 1) a sulfur donor, 2) enhanced adenosine triphosphate (ATP) synthesis, and 3) magnesium.

Zinc sulfate is a component of the composition for two reasons: 1) anion is a sulfur donor, and 2) the metal cation has been used as a cofactor in acne therapy. Although used as a therapeutic modality in the treatment of acne, the requisite dosage has been between 100–135 mg per day of zinc. As with pantothenic acid, efficacy has only been moderate as a single modality of treatment.

Magnesium phosphate tribasic is a phosphate donor therapy facilitating ATP production. It is also a magnesium donor and a reducing agent that facilitates the production of Coenzyme A. Magnesium phosphate therapy decreases the amount of pantothenic acid necessary to result in therapeutic efficacy.

Other vitamins may also prove useful in the treatment of acne in conjunction with the aforementioned substances. These include, but are not limited to, folic acid, pyridoxine and its cogeners vitamin D and it various cogeners, vitamin A or beta carotene and their various cogeners. While, vitamin A has been used in very high doses to treat acne, it is only modestly successful, and since it is fat soluble, toxicity remains an issue. The other noted vitamins facilitate formation of coenzyme A and/or enhance the ability of the skin to resist bacterial invasion.

Finally, as noted previously, thymic peptides such as Fraction 5 (TF5) are extremely useful in a variety of different modalities. TF5 is a partially purified mixture of polypeptides that is routinely prepared from calf thymus glands. However, TF5 may also be prepared from porcine, ovine, murine, goat, rat chicken and human thymus tissues. Preparation and isolation of TF5 has been described (Hooper et al., "The purification and properties of bovine thymosin," *Ann. NY Acad. Sci.* 249:125, 1975). TF5 consists of at least 40 to 50 distinct polypeptides separated by isoelectric focusing on polyacrylamide gel plates (pH 3.5–9.5). TF5 is essentially free of lipids, carbohydrates and endotoxins. TF5 has previously been demonstrated to be effective in reconstituting immune functions in thymic-deprived or immunodeprived animals, in humans with primary immunodeficiencies, and in immunosuppressed cancer patients. An apparent primary effect of this mixture of peptides is to stimulate cell-medicated immunity.

Two of the major biologically active ingredients in TF5 are thymosin $\alpha_1$ (T$\alpha_1$) an immunomodulatory peptide of 28 amino acids (molecular weight 3,108 daltons) (Low et al., "The chemistry and biology of Thymosin I. isolation and characterization and biological activities of T$\alpha_1$ and polypeptide $\beta_1$ from calf thymus," *J. Bio. Chem.* 254:981, 1979) and thymosin $\beta_4$ (T$\beta_4$), an actin-sequestering peptide of 43 amino acids (molecular weight 4,963 daltons) (Low, T. L. K., and Goldstein, A. L., "Chemical characterization of thymosin $\beta_4$," *J. Bio. Chem.* 257:1000, 1982). T$\alpha_1$ and T$\beta_4$ are highly conserved in nature and their amino acid sequences are identical in most mammalian species.

More than a dozen TF5-like preparations have been prepared from calf or porcine thymus tissue. These thymic extracts such as thymostimulin (TP-1), TFX, thymalin, thymoject, thym-Uvocal, and others, are variations of the TF5 formulation and are all partially purified preparations composed primarily of polypeptide mixtures with molecular weights of 15,000 or less. The major biologically active components of TF5 contain T$\alpha_1$ and T$\beta_4$, as well as lower concentrations of other purified will characterized thymosin peptides such as prothymosin a (Pro T$\alpha_1$), T$\alpha_2$ to T$\alpha_{11}$ and T$\beta_3$, T$\beta$ to T$\beta_{13}$, MB 35, MB 40, ubiquitin, thymulin (FTS), thymic humoral factor (THF$\alpha_2$) and thymopoietin (TP). The TF5-like extracts prepared by variations of the procedure used originally to prepare TF5 may also contain α and β as key ingredients and smaller quantities of the other peptides described in TF5 such as Pro Tα$_3$, FTS, THFα$_2$, TP, ubiquitin and MB 35 and MB 40.

The method of the present invention preferably includes a formulation of TF5 and TF5-like thymic peptide extracts that contain Tα$_1$ and/or Tβ$_4$. Tα$_1$ and Tβ$_4$ have been characterized with regard to their ability to stimulate and regulate cell-mediated immunity, to enhance wound healing, and for their ability to increase resistance to microbial infections and to decrease microbial adherence (Baumann et al., Preclinical studies of thymosin α$_1$ and thymosin β$_4$, In: Mauer, H. R., Goldstein, A. L., Hager, E. D., Thymic peptides in preclinical and clinical medicine, W. Zuckschwerdt Verlag Munchen, Bern, Wien, New Your, pp.13–17, 1977). The terms TF5 or TF5-like, as used in the present application, refer only to those thymic extracts that include Tα$_1$ and/or Tβ$_4$. Although other peptides may be present in some concentration in TF5 or TF5-like preparations, the presence of Tα$_1$ and/or Tβ$_4$ in the TF5 or TF5-like preparation is required for use in the present invention, and preferably at a concentration ranging from 0.05 to 0.1% by weight for each Tα$_1$ and/or Tβ$_4$.

The importance of TF5 or TF5-like preparations in preventing infections in immunocompromised patients was first suggested by studies in immunosuppressed animals (Oates, K., Goldstein, A. L., Thymosin. In De Vita, D. T. Hellman, S., Rosenberg, S. A. (eds.), Biological therapy of cancer, 2nd ed., J B Lippencott, Philadelphia, pp. 705–718, 1995; Goldstein, A. L., "Clinical applications of thymosin alpha-1," Cancer Invest. 12:545–547, 1994). Early studies demonstrated an increased survival rate of immunosuppressed mice infected with BCO, Candida, or Cryptococcus when these animals were treated with TF5, Tα$_1$ or TF5-like preparations (Collins, F. M. and Morrison, N. E., "Restoration of T-cell responsiveness by thymosin: Expression of antituberculosis immunity in mouse lungs," Infect. Immun. 23:330, 1979; Bistoni et al., "Increase of mouse resistance to Candida albicans infection by Thymosis α$_1$," Infect. Immun. 36(2):609–614, 1982). In T-cell depleted mice, TF5 has been found to restore cellular immunity to *Blastomyces dermatitidis* (Longley, R. E. and Cozad, G. C., "Thymosin restoration of cellular immunity to *Blastomyces dermatitidis* in T-cell depleted mice," Infect. Immun. 26(1):187-92, 1979). In similar studies cell-mediated immunity to *Listeria monocytogenes* was increased in protein malnourished mice following treatment with TF5. The administration of TF5 or Tα$_1$ also stimulated a significant rise in the amount of interferon (IFN) produced in mice infected with the Newcastle disease virus (Huang et al., "Thymosin treatment modulates production of interferon," J. Interferon Res. 1:411, 1981). In similar studies in mice, an injection of TF5 or Tα$_1$ increased resistance to infection with *Candida albicans* (Bistoni et al., "increase of mouse resistance to *Candida albicans* infection by Thymosin α$_1$," Infect. Immun. 36(2):609–614, 1982; Salvin, S. B. and Neta, R., "Resistance and susceptibility to infection in inbred murine strains. I. Variations in the response to thymic hormones in mice infected with *Candida albicans*," Cell Immunol. 75:160, 1983). The increased resistance to infection with an infections agent after administration of TF5 has been attributed to an increase in the release of specific cytokines such as MIF and IFN (Salvin, S. B. and Neta, R., "Resistance and susceptibility to infection in inbred murine strains. I. Variations in the response to thymic hormones in mice infected with *Candida albicans*," Cell Immunol. 75:160, 1983). Injection of TF5 and Tα1 has also been shown to protect 5-fluorouracil (5FU)- or morphine-immunosuppressed mice against opportunistic infections with *C. albicans, Listeria monocytogenes, Pseudomonas aeruginosa*, and *Serratia marescens* (Ishitsuka et al., "Protective activity of thymosin against opportunistic infections in animal models," Cancer Immunol. Immunother. 14:145, 1983; Di Francesco et al., "Combined effect of flucazole and thymosin oil on systemic candidiasis in mice immunosuppressed by morphine treatments," Clin. Ex. Immuno. 97:347–352, 1994). The efficacy of Tα$_1$ administered in combination with the antiviral drug amantadine and interferon was also demonstrated in mice infected with the influenza virus. This new combination therapy protocol has been found to significantly increase the long term survival, to reduce viral titers in the lungs, and to restore a number of the immunological parameters tested such as natural killer cell activity, cytotoxic T-lymphocyte responses, and subsets of CD4+/CD8+ lymphocytes (D'Agostini et al., "Efficacy of combination therapy with amantadine, Tα$_1$ and α/β IFN in mice infected with influenza A virus," Int. J. Immunopharmacol. 18:95–102, 1996).

Clinical studies in humans using various TF5 or TF5-like preparations (e.g., THF, TFX, TP-1) have shown that the administration of thymic fractions can shorten the course of viral infections (e.g., herpes zoster, herpes simplex, adenovirus, hepatitis, and cytomegalovirus) and increase the restoration of T-cell immunity in these patients (Ajiuti et al., "A placebo controlled trial of thymic hormone treatment of recurrent herpes simplex labialis infection in immunodeficient host: Results after a 1 year follow up," Clin. Immunol. Immunopathol. 30:11, 1984; Businco, L. and Rezza, E., "Therapy of viral disease in immunosuppressed patients with TP-1," Thymic Hormones and T-lymphocytes (A. F. Wigzel, ed.), Academic Press, New York, p. 295, 1981; Demartino et al., "T-lymphocytes in children with respiratory infections: Effect of the use of thymostimulin on the alteration of T-cell subsets," Int. J. Tissue React. 6:223, 1984; Schulof, R. S. and Goldstein, A. L., "Clinical applications of thymosin and other thymic hormones," Recent Advances in Clinical Immunology (R. A. Thompson and N. R. Rose, eds.), Churchill Livingstone, Edinburgh, p. 243, 1983; Trianin et al., "The role of THF a thymic hormone, as a regulator of T-cell differentiation in humans," Current Concepts in Human Immunology and Cancer Immunomodulation (Serrpu et al., eds.), Elsevier Biomedical, New York, p. 295, 1981). These studies suggest that TF5 or TF5-like preparations may be useful in preventing or attenuating infections in immunocompromised hosts.

TF5 and TF5-like preparations have also been utilized, in clinical trials, in patients with primary and secondary immunodeficiencies. A number of syndromes related to congenital defects of the immune system are included in this category. These may include T-cell, B-cell or both lymphocyte population defects. An increase in the percentage and numbers of Erosette-forming cells in vitro after incubation with TF5 and TF5-like preparations has been reported (Schulof, R. S. and Goldstein, A. L., "Clinical applications of thymosisn and other thymic hormones," Recent Advances in Clinical Immunology (R. A. Thompson and N. R. Rose, eds.), Churchill Livingstone, Edinburgh, p. 243, 1983).

Several thymic preparations, such as TF5, TP-1, TP-5, thymulin, THF, and TPX, have been studied in clinical trials in children with primary immunodeficiency diseases (Goldstein, A. L., "Clinical applications of thymosin α$_1$," Cancer Invest. 12:545–547, 1994, Trianin et al., "The role of THF a thymic hormone, as a regulator of T-cell differentiation in humans," Current concepts in Human Immunology and Cancer Immunomodulation (Serrpu et al., eds.), Elsevier Biomedical, New York, p. 295, 1981; Bach, J. F. and Dardenne, M. "Clinical aspects of thymulin (FTS)," *Thymic Hormones and Lymphokines* (A. L. Goldstein, ed.), Plenum Press, New York, p. 593, 1984; Davies, E. G. and Levinsky, R. J., "Experience in the use of thymic hormones for immunodeficiency disorders," *Thymic Factor Therapy*, Vol. 16 (N. A. Byron and J. R. Hobbs, eds.), Serono Symposium Publications, Raven Press, New York, p. 156, 1984; Goldstein, A. L., "thymosin alph-1: [Note: "alph-1" is in original copy.] Chemistry, mechanism of action and clinical applications," *Combination Therapies* 2 (E. Garaci and A. L. Goldstein, eds.), Plenum Press, New York, pp. 39–48, 1993; Skotnicki et al., "Biological properties and clinical use of calf thymus extract TFX-Polfa," *Thymic Hormones and Lymphokines* (A. L. Goldstein, ed.), Plenum Press, New York, p. 545, 1984; Wara et al., "Thymosin fraction 5 therapy in patients with primary immunodeficiency disorders," *Thymic Factor Therapy*, Vol. 16 (N. A. Buron and J. R. Hobbs, eds.), Serono Symposia Publications, Raven Press New York, p. 123, 1984). These studies indicate that thymic fractions are useful in reconstituting cellular immune responses and improving clinical status in these patients.

The $T\alpha_1$ fraction and the $T\beta$ fraction have been completely characterized and are noted for their ability to decrease microbial adherence, enhance wound healing, and stimulate cell-mediated immunity. Thus, topical application of these particular thymic fractions should increase the ability of the skin to resist fungal and other infections, and appear to assist the skin's ability to mount a reaction to fungus and eliminate it. Therefore, TF5 not only enhances healing of existing acne skin lesions but prevents or decreases the infection that typically occurs in conjunction with acne skin lesions and acts to prevent the formation of new lesions. One skilled in the art will note that the amount of TF5 has been increased in this formulation, above levels that have previously been used, to provide the benefits described above.

A topical preparation, according to the present invention, was developed and includes pantothenic acid in an anhydrous epidermalytic vehicle. In and of itself, the preparation was capable of reducing comedone counts as noted in the study that was done. However, as also noted in the study, the combination of the topical and oral preparations was better than either preparation acting alone. A representative formulation is herein described in Table 2.

A study was conducted by a board-certified dermatologist on 30 patients diagnosed with typical acne. Comedone counts were done on all patients at monthly intervals. Ten patients were given the oral supplement alone Ten patients were given the topical treatment alone and ten patients were given a combination of both the topical and oral treatment. Comedone counts were totaled and averaged over the three months that the study was conducted. As can be seen by examination of FIGS. 3–5, in all cases there was surprising reduction in the number of lesions. However, the combination therapy showed a surprising reduction in comedones compared to either preparation alone (more than half that counted using single preparations.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. An orally ingestible composition for the treatment of acne comprising:
   a. Calcium Pantothenate, ranging from 1.0–99 percent by weight;
   b. Riboflavin, ranging from 1.0–99 percent by weight;
   c. Zinc sulfate, ranging from 1.0–99 percent by weight;
   d. Magnesium Phospate Tribasic, ranging from 1.0–99 percent by weight;
   e. Folic Acid, ranging from 1.0–99 percent by weight;
   f. Pyridoxine, ranging from 1.0–55 percent by weight;
   g. Vitamin D, ranging from 0.001–50 percent by weight;
   h. Vitamin A, ranging from 0.001–50 percent by weight; and
   i. Thymosin Fraction 5, ranging from 0.001–85 percent by weight.

2. The composition for the treatment of acne according to claim 1 wherein the
   a. Calcium Pantothenate, is approximately 71.43 percent by weight;
   b. Riboflavin, is approximately 2.38 percent by weight;
   c. Zinc sulfate, is approximately 4.77 percent by weight;
   d. Magnesium Phospate Tribasic, is approximately 9.54 percent by weight;
   e. Folic Acid, is approximately 9.54 percent by weight;
   f. Pyridoxine, is approximately 0.95 percent by weight;
   g. Vitamin D, is approximately 0.026 percent by weight;
   h. Vitamin A, is approximately 0.069 percent by weight; and
   i. Thymosin Fraction 5, is approximately 1.19 percent by weight.

3. A method for the oral treatment of acne comprising the step of providing a composition that increases formation of Acetyl Coenzyme A, wherein the composition is designed to be ingested by an individual for treatment of acne.

4. The method according to claim 3 wherein the composition that increases formation of Acetyl Coenzyme A is comprised of at least thymosin fraction 5.

5. The method according to claim 4 further wherein the composition that increases the formation of Acetyl Coenzyme A is further comprised of zinc, pantothenic acid, magnesium, pyridoxine, vitamins A and D, riboflavin, and folic acid.

6. The method according to claim 3 wherein the composition that increases the formation of acetyl Coenzyme A has is comprised of a. Calcium Pantothenate, ranging from 1.0–99 percent by weight;
b. Riboflavin, ranging from 1.0–99 percent by weight;
c. Zinc sulfate, ranging from 1.0–99 percent by weight;
d. Magnesium Phospate Tribasic, ranging from 1.0–99 percent by weight;
e. Folic Acid, ranging from 1.0–99 percent by weight;
f. Pyridoxine, ranging from 1.0–55 percent by weight;
g. Vitamin D, ranging from 0.001–50 percent by weight;
h. Vitamin A, ranging from 0.001–50 percent by weight; and
i. Thymosin Fraction 5, ranging from 0.001–85 percent by weight.

7. The method according to claim 6 wherein the
a. Calcium Pantothenate, is approximately 71.43 percent by weight;
b. Riboflavin, is approximately 2.38 percent by weight;
c. Zinc sulfate, is approximately 4.77 percent by weight;
d. Magnesium Phospate Tribasic, is approximately 9.54 percent by weight;
e. Folic Acid, is approximately 9.54 percent by weight;
f. Pyridoxine, is approximately 0.95 percent by weight;
g. Vitamin D, is approximately 0.026 percent by weight;
h. Vitamin A, is approximately 0.069 percent by weight; and
i. Thymosin Fraction 5, is approximately 1.19 percent by weight.

8. A method for the topical and oral treatment of acne comprising the step of providing an oral composition that increases formation of Acetyl Coenzyme A, and providing a topical composition comprising pantothenic acid in an anhydrous transport vehicle.

9. The method according to claim 8 wherein the composition that increases formation of Acetyl Coenzyme A is comprised of at least thymosin fraction 5.

10. The method according to claim 9 further wherein the composition that increases the formation of Acetyl Coenzyme A is further comprised of zinc, pantothenic acid, magnesium, pyridoxine, vitamins A and D, riboflavin, and folic acid.

11. The method according to claim 8 wherein the composition that increases the formation of acetyl Coenzyme A has is comprised of
a. Calcium Pantothenate, ranging from 1.0–99 percent by weight;
b. Riboflavin, ranging from 1.0–99 percent by weight;
c. Zinc sulfate, ranging from 1.0–99 percent by weight;
d. Magnesium Phospate Tribasic, ranging from 1.0–99 percent by weight;
e. Folic Acid, ranging from 1.0–99 percent by weight;
f. Pyridoxine, ranging from 1.0–55 percent by weight;
g. Vitamin D, ranging from 0.001–50 percent by weight;
h. Vitamin A, ranging from 0.001–50 percent by weight; and
i. Thymosin Fraction 5, ranging from 0.001–85 percent by weight.

12. The method according to claim 11 wherein the
a. Calcium Pantothenate, is approximately 71.43 percent by weight;
b. Riboflavin, is approximately 2.38 percent by weight;
c. Zinc sulfate, is approximately 4.77 percent by weight;
d. Magnesium Phospate Tribasic, is approximately 9.54 percent by weight;
e. Folic Acid, is approximately 9.54 percent by weight;
f. Pyridoxine, is approximately 0.95 percent by weight;
g. Vitamin D, is approximately 0.026 percent by weight;
h. Vitamin A, is approximately 0.069 percent by weight; and
i. Thymosin Fraction 5, is approximately 1.19 percent by weight.

13. The method according to claim 8 wherein the pantothenic acid containing topical composition is comprised of:
a. Pantothenic acid, ranging from 0.01–80 percent by weight;
b. Urea, ranging from 0.02–50 percent by weight;
c. Urea Peroxide, ranging from 0.01–50 percent by weight;
d. Propylene glycol, ranging from 1–99 percent by weight;
e. Phenoxyethanol, ranging from 0–80 percent by weight; and
f. Fraction 5, ranging from 0.001–50 percent by weight.

14. The method according to claim 13 wherein the
a. Pantothenic acid is approximately 2 percent by weight;
b. Urea is approximately 10 percent by weight;
c. Urea Peroxide is approximately 2 percent by weight;
d. Propylene glycol is approximately 82.75 percent by weight;
e. Phenoxyethanaol is approximately 3 percent by weight; and
f. Fraction 5 is approximately 0.25 percent by weight.

15. The method according to claim 11 wherein the pantothenic containing topical composition is comprised of:
a. Pantothenic acid, ranging from 0.01–80 percent by weight;
b. Urea, ranging from 0.02–50 percent by weight;
c. Urea Peroxide, ranging from 0.01–50 percent by weight;
d. Propylene glycol, ranging from 1–99 percent by weight;
e. Phenoxyethanaol, ranging from 0–80 percent by weight; and
f. Fraction 5, ranging from 0.001–50 percent by weight.

16. The method according to claim 15 wherein the
a. Pantothenic acid is approximately 2 percent by weight;
b. Urea is approximately 10 percent by weight;
c. Urea Peroxide is approximately 2 percent by weight;
d. Propylene glycol is approximately 82.75 percent by weight;
e. Phenoxyethanaol is approximately 3 percent by weight; and
f. Fraction 5 is approximately 0.25 percent by weight.

17. The method according to claim 12 wherein the pantothenic containing topical composition is comprised of:
a. Pantothenic acid, ranging from 0.01–80 percent by weight;
b. Urea, ranging from 0.02–50 percent by weight;
c. Urea Peroxide, ranging from 0.01–50 percent by weight;
d. Propylene glycol, ranging from 1–99 percent by weight;

e. Phenoxyethanaol, ranging from 0–80 percent by weight; and f. Fraction 5, ranging from 0.001–50 percent by weight.

18. The method according to claim 17 wherein the a. Pantothenic acid is approximately 2 percent by weight;

b. Urea is approximately 10 percent by weight;

c. Urea Peroxide is approximately 2 percent by weight;

d. Propylene glycol is approximately 82.75 percent by weight;

e. Phenoxyethanaol is approximately 3 percent by weight; and f. Fraction 5 is approximately 0.25 percent by weight.

* * * * *